US008423158B2

United States Patent
Jolly et al.

(10) Patent No.: US 8,423,158 B2
(45) Date of Patent: Apr. 16, 2013

(54) MULTICHANNEL CYLINDRICAL ELECTRODE FOR NERVE STIMULATION AND RECORDING

(75) Inventors: Claude Jolly, Innsbruck (AT); Anandhan Dhanasingh, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/325,176

(22) Filed: Dec. 14, 2011

(65) Prior Publication Data

US 2012/0158112 A1    Jun. 21, 2012

Related U.S. Application Data

(60) Provisional application No. 61/423,181, filed on Dec. 15, 2010.

(51) Int. Cl.
*A61N 1/05*    (2006.01)

(52) U.S. Cl.
USPC ............................. 607/137; 607/56; 607/57

(58) Field of Classification Search ............... 607/56, 607/57, 137
See application file for complete search history.

(56) References Cited

U.S. PATENT DOCUMENTS 7,894,910 B2 *   2/2011   Cowan et al. .................. 607/57

\* cited by examiner

*Primary Examiner* — Christopher D Koharski
*Assistant Examiner* — Michael Carey
(74) *Attorney, Agent, or Firm* — Sunstein Kann Murphy & Timbers LLP

(57) ABSTRACT

An implantable multi-channel electrode is described. An ear implant electrode with a cylinder shaped electrode body has opposing top and bottom end surfaces. Electrode contacts are dispersed across the bottom end surface to provide electrical interaction with nearby auditory nerve tissue.

17 Claims, 5 Drawing Sheets

MULTICHANNEL CYLINDRICAL ELECTRODE FOR NERVE STIMULATION AND RECORDING

This application claims priority from U.S. Provisional Patent Application 61/423,181, filed Dec. 15, 2011; incorporated herein by reference.

TECHNICAL FIELD

The present invention relates to an implantable electrode for biomedical devices.

BACKGROUND ART

A normal ear directs sounds as shown in FIG. 1 from the outer ear pinna 101 through the generally cylindrical ear canal 110 to vibrate the tympanic membrane 102 (eardrum). The tympanic membrane 102 moves the bones of the middle ear 103 that vibrate the cochlea 104, which in turn functions as a transducer to generate electric pulses to the brain that are interpreted as sounds. In addition, the inner ear also includes a balance sensing vestibular system which involves the vestibular labyrinth 105, its three interconnected and mutually orthogonal semi-circular canals: the superior canal 106, posterior canal 107, and horizontal canal 108 (as well as the otolith organs, the utricle and saccule—not shown). The canals and spaces of the vestibular labyrinth 105 are filled with endolymph fluid which moves relative to head movements, thereby activating hair cells that send an electrical balance signal to the brain via the vestibular nerve 111.

In some people, the vestibular system is damaged or impaired, causing balance problems such as unsteadiness, vertigo and unsteady vision. Vestibular implants are currently under development, with one of the challenges being to stimulate the fibers of the vestibular nerve 111, which lie embedded in a plane in a bony channel surrounding the vestibular labyrinth 105. These nerve fibers need to be stimulated at several different specific locations, suggesting use of a multi channel electrode.

The electrode contacts of such a multi channel electrode need to be as close as possible to the nerve fiber, but yet still some distance away, for example, a few microns up to some tens of microns away from the nerve fibers. To surgically approach the nerve fibers, some of the surrounding bone may be drilled away until a membranous periosteum is exposed, thereby creating an electrode well just above the plane of the nerve fibers. The electrode well may be conical in shape due to the spherical drill burr, 100 microns to 1 mm or more in depth. Or the electrode well may be extended in some lateral direction creating a shoe box-shape well.

Once an electrode well has been surgically prepared, a multi channel electrode with a collection of electrode contacts needs to be placed in it. A planar shape electrode could be used, but it would need to be extremely flexible and yet robust enough to adapt to the shape of the electrode well. And the connection between the electrode contacts and the bottom of the electrode well may be less than optimum with a planar electrode. The placement of a planar electrode in the electrode well also may be hindered by the electrode lead that connects the electrode contacts to the implanted stimulator device.

SUMMARY

Embodiments of the present invention are directed to an implantable multi-channel electrode. An ear implant electrode with a cylinder shaped electrode body has opposing top and bottom end surfaces. Electrode contacts are dispersed across the bottom end surface to provide electrical interaction with nearby auditory nerve tissue.

In specific embodiments there may also be at least one ground electrode around an outer circumference of the electrode body providing an electrical circuit reference for the electrode contacts. Or there may be a ground electrode in the bottom end surface, for example, around the outer circumference. Or there may be multiple ground electrodes, for example, one adjacent to each electrode contact.

An insertion limiter may be located on an outer circumference of the electrode body limiting how closely the electrode body may be positioned with respect to the nerve tissue. For example, the insertion limiter may be multiple insertion protrusions disposed around at least a portion of the outer circumference. Or the insertion limiter may be a skirt protrusion structure extending around at least a portion of the outer circumference.

There may be an electrode lead connected to and much smaller than the electrode body to provide electrical connection of the electrode contacts to an implant stimulator device. The electrode lead may be connected to the top end surface of the electrode body. Or the electrode body may include a cylindrical side surface where the electrode lead is connected. The cylinder shape may specifically be a circular cylinder, an elliptic cylinder, or a multi-lobe cylinder shape. The electrode body may be adapted to fit into a prepared electrode holding recess adjacent to the nerve tissue. The bottom end surface may be planar or curved. The electrode body may be made of a resilient silicone material.

Embodiments of the present invention also include a biomedical implant system such as a vestibular implant system having an implantable multi-channel electrode according to any of the foregoing.

DETAILED DESCRIPTION

Embodiments of the present invention are directed to an implantable multi-channel electrode in the form of an ear implant electrode with a cylinder shaped electrode body having opposing top and bottom end surfaces. The electrode contacts are dispersed across the bottom end surface of the electrode body to provide electrical interaction with nearby nerve tissue. Such a small cylindrical multi-channel electrode is useful to stimulate small nerve fibers which lie very close together. A multi-channel ear implant electrode can also allow choosing the best electrode contacts closest to the nerve cells for use in stimulation. In the past, this has proven to be quite difficult with the small vestibular nerve and a single channel electrode where interaction of the electrode with the nerve is hit or miss based on its proximity to the nerve, where a miss means no stimulation is possible.

Figure 1:
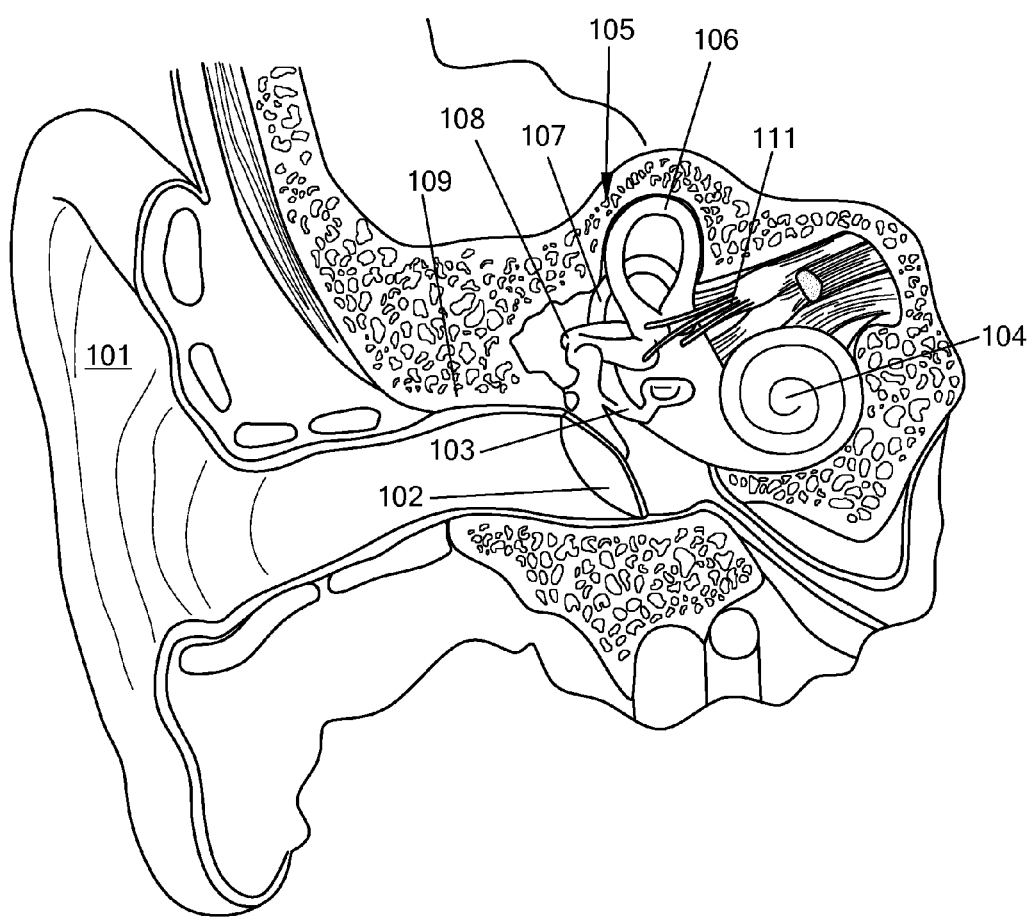
FIG. 1 shows the anatomy of a normal human ear including structures of the vestibular system.
Figure 2:
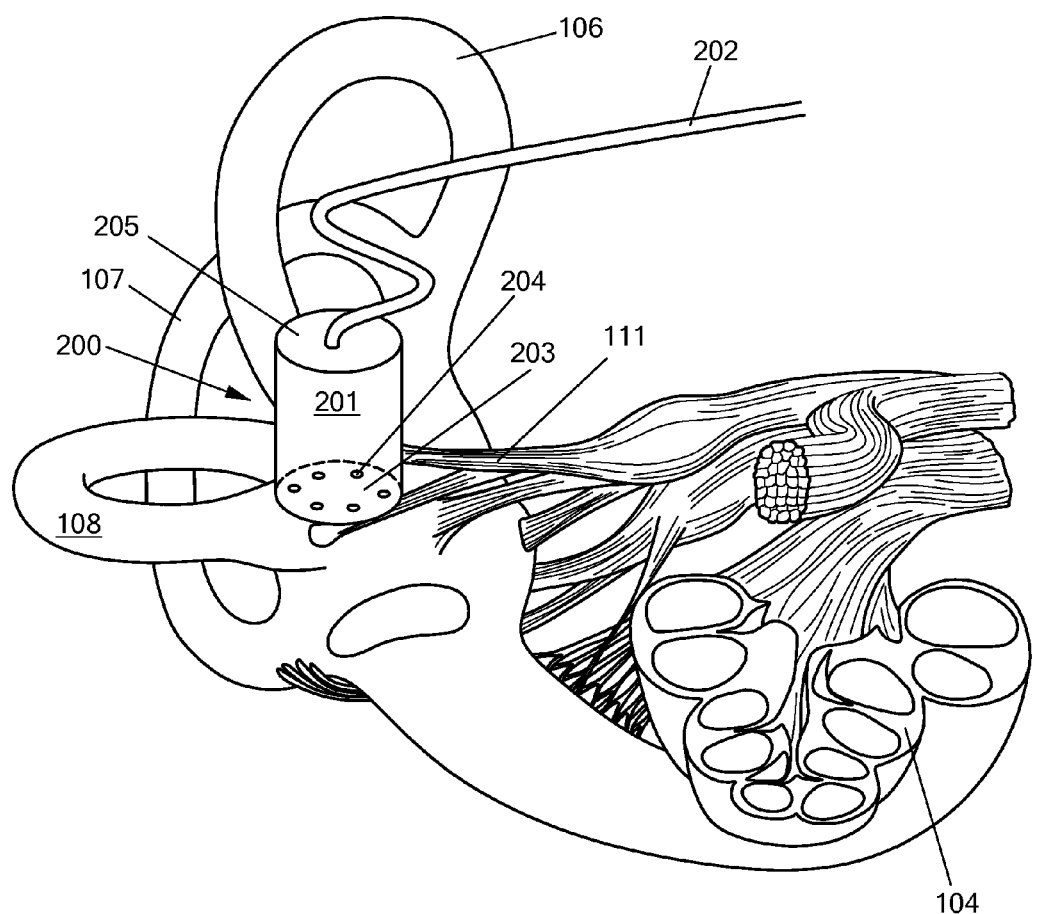
FIG. 2 shows an example of a multi-channel implant electrode according to one embodiment of the present invention when positioned for use in a vestibular implant system.

FIG. 2 shows an example of a multi-channel ear implant electrode 200 according to one embodiment of the present invention when positioned for use in a vestibular implant system. The cylinder shaped electrode body 201 is implanted so that the electrode contacts 204 on its bottom end surface 203 are positioned adjacent to the nerve fibers of the vestibular nerve 111 where they connect to the vestibular labyrinth. The electrode body 201 may be made of resilient silicone material of a size and shape specifically adapted to fit properly in the drilled electrode well.

Figure 6:
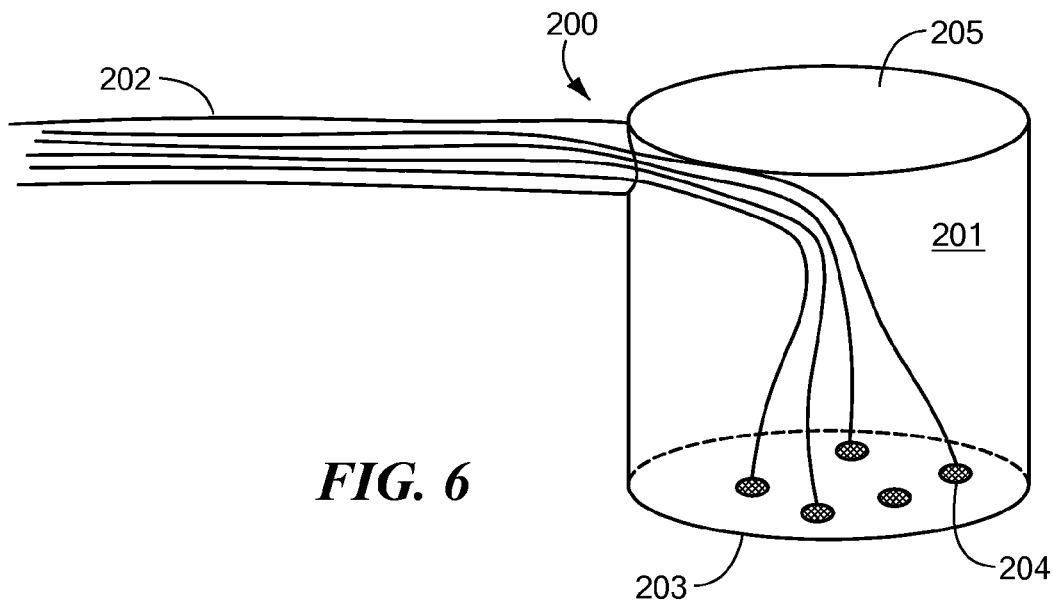
FIG. 6 shows a cylindrical shaped electrode with an electrode lead that enters from the side.

An electrode lead 202 much smaller in diameter than the electrode body 201 is connected to the top end surface 205 of the electrode body 201 and provides electrical connection of the electrode contacts 204 to an implant stimulator device. This arrangement results in low drag forces on the electrode body 201. Locating the connection of the electrode lead 202 at the top end surface 205 of the electrode body 201 on the opposite end from the bottom end surface 203 of the electrode contacts 204 minimizes its effect on the interaction of the electrode contacts 204 with the nerve fibers. By contrast, placing the electrode lead 202 on the side of the electrode body 201 as with a conventional flat planar electrode would require additional insertion space and be destabilizing for the implanted placement of the electrode body 201. On the other hand, FIG. 6 shows an embodiment of a cylinder shaped electrode body 201 with an electrode lead 202 that enters the side of the electrode body 201. Such an embodiment might be especially useful, for example, in an application as a transcranial plug that penetrates through the skull bone with electrode contacts 204 that lie against target tissue on the surface of the brain.

Figure 7A:
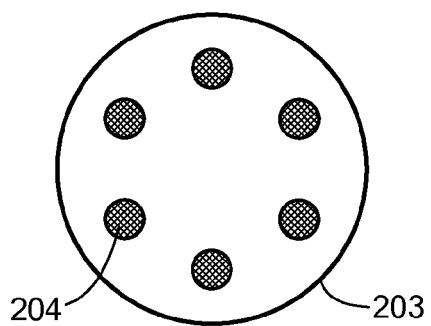
FIG. 7 A-C shows the bottom end surface of electrodes having different specific cylindrical shapes.
Figure 7B:
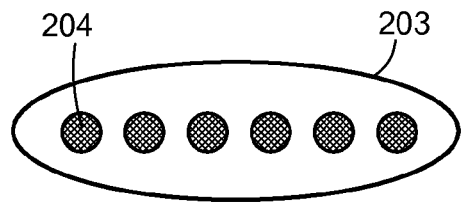
Figure 7C:
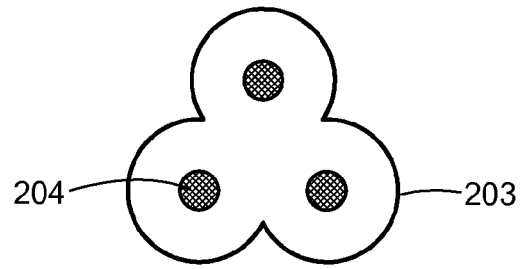

FIG. 7A shows the bottom end surface 203 of a specific embodiment of an ear implant electrode 200 where the electrode body 201 is a circular cylinder where the electrode contacts 204 are distributed towards the outer circumference. FIG. 7B shows the bottom end surface 203 where the electrode body 201 is an elliptic cylinder and the electrode contacts 204 are distributed in a straight line along the length of the elliptical axis. Such a shape may allow less bone to be removed at the insertion point. FIG. 7C shows the bottom end surface 203 where the electrode body 201 is a multi-lobed cylinder with an electrode contact 204 in each lobe. In specific embodiments, the bottom end surface 203 may be planar, curved, etc.

Figure 3A:
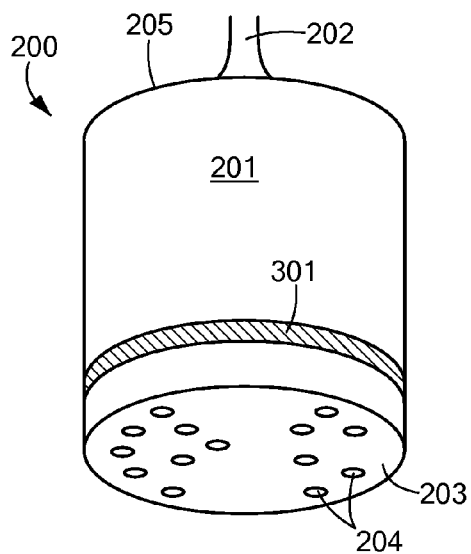
FIG. 3 A-D shows embodiments of an electrode having a ground electrode.
Figure 3B:
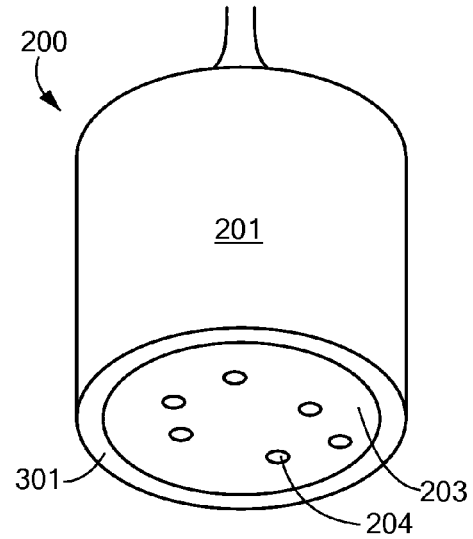
Figure 3C:
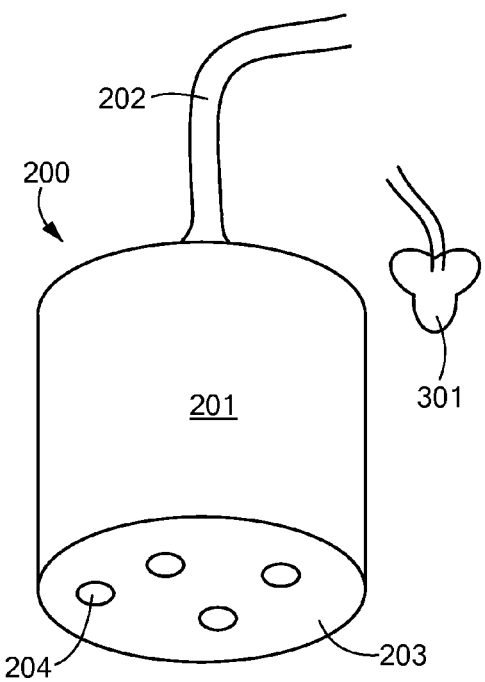
Figure 3D:
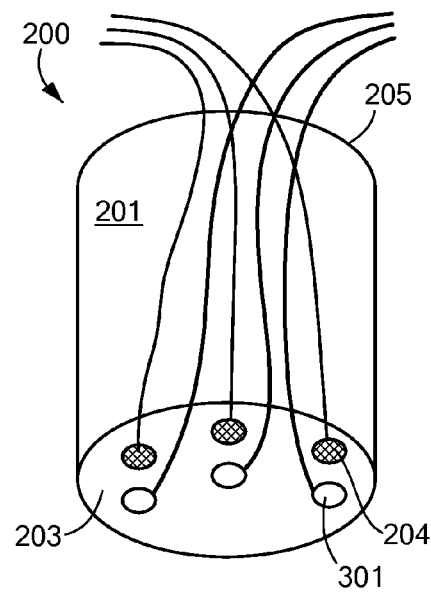

FIG. 3A shows a bottom perspective view of an ear implant electrode 200 having a ground electrode 301 around the outer circumference of the electrode body 201 some distance above the bottom end surface 203. The ground electrode 301 provides an electrical circuit reference for the electrode contacts 204 on the bottom surface 203. Locating a ground electrode 301 this way helps confine the electrical field from the stimulation signals to the region around the cylinder of the electrode body 201 and reduces current dispersion and unwanted stimulation of nearby nerve cells. FIG. 3B shows an example of another embodiment wherein there is a ground electrode 301 around the outer circumference of the bottom end surface 203. FIG. 3C shows an embodiment having a separate common ground electrode 301. FIG. 3D shows an embodiment where there is an individual ground electrode 301 for each stimulating electrode contact 204. Such an arrangement of adjacent contact pairs helps minimize channel cross-talk—in applications such as vestibular implants this is an important consideration to preserve proper functionality of nearby systems such as the eye.

Figure 4:
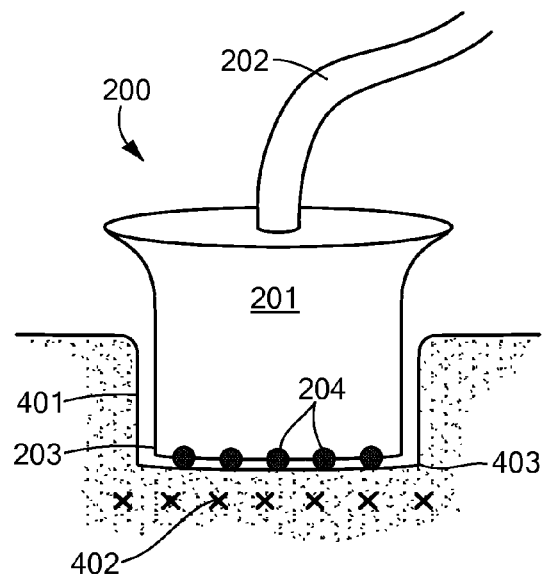
FIG. 4 shows an electrode implanted in an electrode well in a prepared bone location.

FIG. 4 shows an electrode body 201 implanted in an electrode well 401 in a prepared bone location. The bottom end surface 203 of the electrode body 201 fits snuggly against the well bottom 403 of the electrode well 401 so that the electrode contacts 204 are adjacent to the plane of the nerve fibers 402. In specific embodiments, the electrode body 201 may just fit within the electrode well 401, or there may be some compression of the electrode body 201 to fit it more snuggly.

In the embodiment shown in FIG. 4, the electrode contacts 204 are spherical shaped, whereas in the embodiments shown in FIGS. 3 A-D they are flat circles. In other specific embodiments, the electrode contacts 204 may have other specific shapes, for example linear line segments, wire ends, etc.

Figure 5A:
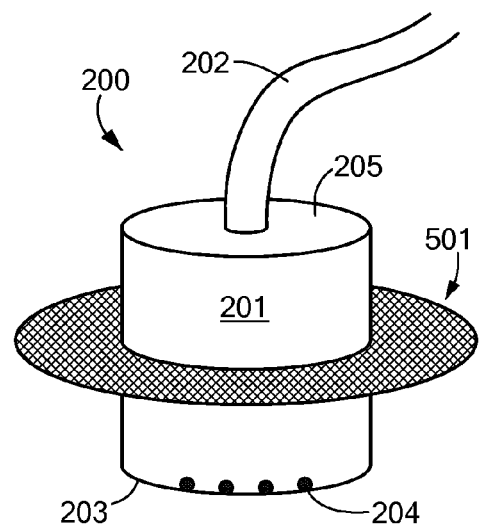
FIG. 5 A-C shows an electrode with an insertion limiter structure.
Figure 5B:
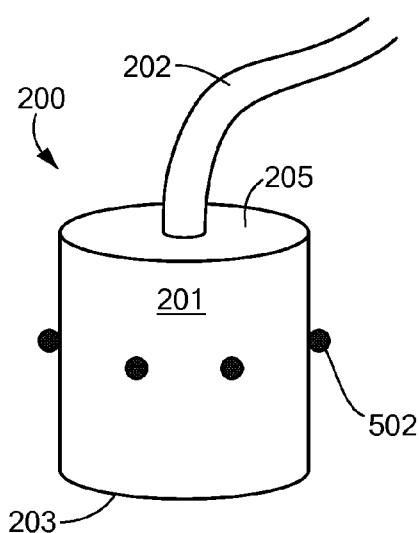
Figure 5C:
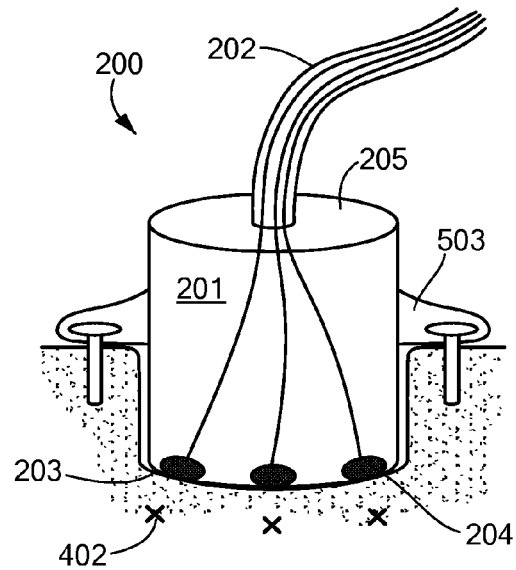

Specific embodiments of such ear implant electrodes 200 may also include one or more insertion limiter structures for limiting how closely the electrode body may be positioned with respect to the nerve tissue. For example, FIG. 5A shows an embodiment of an ear implant electrode 200 having a skirt limiter 501 extending around the outer circumference of the electrode body 201 some height above the bottom end surface 203. The insertion skirt 501 limits how closely the electrode body 201 may be positioned with respect to the nerve tissue. The insertion skirt 501 also provides anchoring stabilization around the cylindrical electrode body 201. FIG. 5B shows an embodiment where there are a plurality of limiter protrusions 502 disposed around at least a portion of an outer circumference of the electrode body 201. FIG. 5C shows an embodiment of a cylindrical multi-channel ear implant electrode having a partial limiting insertion skirt 503 extending part way around the outer circumference of the electrode body 201. Such an embodiment may provide a better field of view during surgical insertion.

Embodiments of a multi-channel cylindrical electrode such as those described above may be very useful when implemented as a small structure for stimulating nerve fibers that are hidden in or shielded by bone, such as is the case with vestibular nerves. The superior and lateral ampullar nerve can be independently stimulated with an optimum contact closest to each nerve. In addition to vestibular system applications, an arrangement of multiple cylindrical multi-channel electrodes may also be useful when connected to one or more stimulation devices to approach a single larger nerve such as in some spinal cord applications, especially to avoid damaging the dura and/or for localized stimulation Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable multi-channel electrode comprising:
   an ear implant electrode with a cylinder shaped electrode body having opposing top and bottom end surfaces; and
   a plurality of electrode contacts dispersed across the bottom end surface and providing electrical interaction with nearby auditory nerve tissue.

2. An electrode according to claim 1, further comprising:
   at least one ground electrode providing an electrical circuit reference for the electrode contacts.

3. An electrode according to claim 2, wherein the ground electrode is positioned around an outer circumference of the electrode body.

4. An electrode according to claim 2, wherein the ground electrode is positioned in the bottom surface of the electrode body.

5. An electrode according to claim 2, wherein the ground electrode includes a plurality of ground electrode contacts.

6. An electrode according to claim 1, further comprising:
an insertion limiter located on an outer circumference of the electrode body for limiting how closely the electrode body may be positioned with respect to the nerve tissue.

7. An electrode according to claim 6, wherein the insertion limiter is a skirt protrusion structure extending around at least a portion of an outer circumference of the electrode body.

8. An electrode according to claim 6, wherein the insertion limiter is a plurality of limiter protrusions disposed around at least a portion of an outer circumference of the electrode body.

9. An electrode according to claim 1, further comprising:
an electrode lead connected to and much smaller than the electrode body and providing electrical connection of the electrode contacts to an implant stimulator device.

10. An electrode according to claim 9, wherein the electrode lead is connected at the top end surface of the electrode body.

11. An electrode according to claim 1, wherein the electrode body is adapted to fit into a prepared electrode holding recess adjacent to the nerve tissue.

12. An electrode according to claim 1, wherein the electrode body is made of a resilient silicone material.

13. An electrode according to claim 1, wherein the electrode body has a circular cylinder shape.

14. An electrode according to claim 1, wherein the electrode body has an elliptic cylinder shape.

15. An electrode according to claim 1, wherein the electrode body has a multi-lobed cylinder shape.

16. An electrode according to claim 1, wherein the bottom end surface is planar.

17. An electrode according to claim 1, wherein the bottom end surface is curved.

* * * * *